United States Patent
Reynaud et al.

(10) Patent No.: US 7,413,964 B2
(45) Date of Patent: Aug. 19, 2008

(54) METHOD OF REVEALING CRYSTALLINE DEFECTS IN A BULK SUBSTRATE

(75) Inventors: Patrick Reynaud, Saint Martin D'Heres (FR); Oleg Kononchuk, Grenoble (FR); Christophe Maleville, La Terrasse (FR)

(73) Assignee: S.O.I.Tec Silicon on Insulator Technologies, Bernin (FR)

( * ) Notice: Subject to any disclaimer, the term of this patent is extended or adjusted under 35 U.S.C. 154(b) by 169 days.

(21) Appl. No.: 11/481,691

(22) Filed: Jul. 5, 2006

(65) Prior Publication Data

US 2007/0231932 A1     Oct. 4, 2007

(30) Foreign Application Priority Data

Mar. 31, 2006     (FR)     .................................. 06 02786

(51) Int. Cl.
    *H01L 21/30*     (2006.01)
(52) U.S. Cl. ...................................................... 438/455
(58) Field of Classification Search ........................ None
    See application file for complete search history.

(56) References Cited

U.S. PATENT DOCUMENTS

| | | | | |
|---|---|---|---|---|
| 5,961,713 | A | 10/1999 | Wijaranakula | 117/2 |
| 6,146,911 | A | 11/2000 | Tsuchiya et al. | 438/14 |
| 6,548,886 | B1* | 4/2003 | Ikari et al. | 257/610 |
| 2002/0167661 | A1 | 11/2002 | Yagi | 356/237.3 |
| 2004/0003769 | A1* | 1/2004 | Tamatsuka et al. | 117/13 |
| 2004/0183133 | A1* | 9/2004 | Takafuji et al. | 257/347 |
| 2004/0194692 | A1 | 10/2004 | Nishikawa et al. | 117/84 |
| 2005/0039671 | A1 | 2/2005 | Watanabe et al. | 117/19 |
| 2005/0064632 | A1 | 3/2005 | Sakurada et al. | 438/149 |
| 2005/0120944 | A1 | 6/2005 | Hong et al. | 117/13 |
| 2005/0130394 | A1* | 6/2005 | Falster | 438/480 |
| 2006/0283374 | A1 | 12/2006 | Ammon et al. | 117/13 |

FOREIGN PATENT DOCUMENTS

| | | |
|---|---|---|
| DE | 221 308 A1 | 4/1985 |
| EP | 1 158 581 A1 | 11/2001 |
| JP | 2005039671 | 2/2005 |
| JP | 2005159013 A | 6/2005 |
| WO | WO 2004/090516 A1 | 10/2004 |

OTHER PUBLICATIONS

H. Moriceau et al., "A New Characterization Process Used To Qualify SOI Films", Electrochemical Society Proceedings, vol. 99-3, pp. 173-178 (1999).
Search report from French priority application No. 0602786 dated Nov. 1, 2006.

\* cited by examiner

*Primary Examiner*—Scott B. Geyer
*Assistant Examiner*—Andre' Stevenson
(74) *Attorney, Agent, or Firm*—Winston & Strawn LLP

(57) ABSTRACT

This invention provides methods for predictively revealing, in bulk silicon substrates, latent crystalline defects in bulk silicon substrates that become apparent only after subsequent processing, e.g., after processing during which multiple layers are split and lifted from the bulk substrates. Preferred predictive methods include a revealing heat treatment of bulk substrates conducted in a non-reducing atmosphere at a temperature in the range from approximately 500° C. to 1300° C. If desired, a further revealing heat treatment or defect enlargement step can be performed to enlarge defects revealed by the first revealing heat treatment.

23 Claims, 1 Drawing Sheet

METHOD OF REVEALING CRYSTALLINE DEFECTS IN A BULK SUBSTRATE

FIELD OF THE INVENTION

The present invention relates to methods for revealing crystalline defects present within a bulk silicon substrate, more particularly, to methods for revealing defects that exist in a latent state in a substrate but that appear when the substrate is subsequently processed. The invention also relates to substrates with low defect densities which are therefore particularly suitable for subsequent processing, e.g., including multiple surface layer transfers.

BACKGROUND OF THE INVENTION

Substrates used in the electronics, optics, and optoelectronics fields are often fabricated from a starting material that is obtained on an industrial scale in the form of ingots. Various ingot fabrication methods (e.g., ingot pulling methods) are known including the Czochralski pulling method (CZ pulling) and the zone melting method (FZ pulling). These methods produce various shapes of ingots of unrefined material, in particular ingots in the shape of a cylinder having two ends that are substantially conical. A silicon ingot may be approximately 1 m to 2 m long.

Such ingots are then cut to eliminate pointed ends, their central cylindrical portion segmented into a plurality of segments, and each segment sliced into a plurality of wafers. Each wafer is finished by, e.g., grinding and polishing, so that its two opposite faces are flat, and then by, e.g., chemical etching steps, so that dust, residual particles, and zones damaged during the preceding material-removal steps are eliminated. Finished wafers are referred to herein "bulk virgin substrates" or "bulk silicon substrates". For example, a 300 mm diameter ingot is generally cut into 20 cm to 30 cm segments and approximately 200 bulk virgin substrates are obtained from each segment, while a 200 mm diameter ingot is cut into 30 cm to 40 cm segments and 200 or more bulk virgin substrates are obtained from each segment.

Each bulk virgin substrate may then be used for further fabricate of, e.g., silicon on insulator ("SOI") wafers. Generally, a SOI type substrate is fabricated by splitting a thin surface layer off a bulk silicon substrate, termed the "donor", and transferring the split layer onto a substrate, termed the "receiver", after interposing a layer of silicon oxide. After transferring a first layer, a donor substrate can be recycled, i.e., a further thin layer is split therefrom and transferred to a second receiver substrate. Such a substrate is termed a "recycled bulk substrate" in the remainder of the description and claims. A donor substrate may be recycled three or four times.

The quality of the transferred layers, and of the final hybrid substrates from which electronic components are fabricated, depends essentially on the quality of bulk substrates. However, bulk substrate often have crystalline defects, which, depending on their number and location, can render it unsuitable for subsequent fabrication. Crystalline defects include: dislocations and voids, which may be isolated or form clusters; agglomerations of interstitial or void type point defects; stacking defects; oxygen precipitates; amorphous or crystalline inclusions of foreign phases (e.g., suicides); metallic precipitates; crystal originated particles (COP); and so forth. COP type defects present in the bulk substrate appear on the transferred layers.

Methods have been developed with the aim of reducing or eliminating defects. See, e.g., EP-A-1 158 581. CZ ingot pulling methods have also been improved to avoid COPs or other types of crystalline defects. U.S. publication 2005/0064632 describes a technique, termed the "copper deposition method", for making defects more apparent in order to characterize and for select wafers suitable for the SOI fabrication. That technique consists in forming a film of oxide at a predetermined depth from the surface of a wafer, removing a portion of the oxide, depositing a solution of copper electrolytes onto the wafer, and applying an electric current. Cu ions then precipitate in regions where the oxide layer is degraded, said regions corresponding to defect zones in the underlying wafer.

Even when using methods to fabricate improved ingots and methods for limiting defects, however, it has been observed that defects still exist and in a latent state that cannot be revealed by current techniques. Especially important is an ability to detect latent crystalline defects which subsequently appear after recycling a wafer several times. There is an economic advantage of being able to predict the quality of bulk substrates before using them in the production line, especially of being able to predict defects which appear only after recycling several times.

SUMMARY OF THE INVENTION

This invention is based on the discovery that defects which are latent in a bulk virgin substrate can be revealed before it is used for the first time, and it provides methods for analyzing bulk silicon (virgin) substrates which, in a predictive manner, reveal small defects which might appear only after recycling that substrate several times. Using these methods bulk substrates revealed to have inappropriate latent defects, defects that can subsequently cause electronic compounds fabricated therefrom to be defective, can be identified. The invention is of particular application to the selection of virgin bulk silicon substrates suitable for fabrication into SOI type substrates, e.g., using transfer techniques known as the SMART CUT® method. This method generally comprises oxidizing at least a first surface of a bulk substrate to form an insulation layer, implanting atomic species into the bulk substrate to form a zone of weakness that defines a useful layer to be transferred with the insulation layer, bonding the insulation layer of the bulk substrate to a receiving substrate; and detaching the useful layer and insulation layer at the zone of weakness to transfer those layers to the receiving substrate. The detaching is preferably achieved by thermal splitting of the zone of weakness.

The invention can be used to deduce the quality of segments cut from ingots, and moreover to decide whether virgin substrates should be cut from the segment, or if such substrates have already been fabricated, to decide whether they should be retained in a production line. After cutting a segment, one or more wafers (or substrates) are preferably lifted from each of its ends, and the methods of the invention are performed to reveal latent defects in the end substrates (referred to herein as "reference substrates"). It should be noted that the sample substrate to which the method of the invention is applied cannot subsequently be used in a layer transfer method. The quality of other substrates from the same segment of an ingot can be inferred from analysis of a few sample (reference) substrates.

The invention can also be used in a production line to analyze a bulk silicon substrate that has already been recycled several times and to determine whether it is of sufficient quality to be recycled again. The quality of bulk substrates can be determined at regular intervals, for example, every three or four recycles, and if it is found that the determined quality is falling off, then the bulk silicon substrates derived from the same segment can be removed from the production line. Thereby, selected bulk silicon (virgin) substrates can be reliably multiply recycled two, three or as many as ten times.

The invention can also be used to develop improved pulling methods so as to obtain substrates having properties required by the final applications. It is known that the quality of a bulk virgin substrate is strongly linked to the type of pulling method used to fabricate it and to the conditions under which that method has been preformed. The effects of these pulling conditions can be analyzed by applying the methods of this invention to sample bulk virgin substrates from sample ingots.

Further, the methods of the invention are simple and inexpensive to carry out, and allow virgin substrates, or substrates that have already been recycled, to be analyzed. They allow quality control to be performed.

In a preferred embodiment, defect revealing methods comprise a "revealing heat treatment" step during which a bulk substrate to be analyzed is subject to a revealing heat treatment. In one embodiment, the revealing heat treatment is performed in a non-reducing atmosphere at a temperature in the range from approximately 500° C. to 1300° C. More preferably, the revealing heat treatment is carried out at a temperature close to 950° C. for approximately 6 hr. In another embodiment, the revealing heat treatment can be performed in a vessel containing a gas comprising at least 10 ppm of oxygen (based on the whole volume of the gas mixture present in the vessel) mixed with argon or nitrogen, or a mixture of the two, for a period of at least 3 minutes. Alternatively, the revealing heat treatment can be preceded by a dry oxidation step and can be performed in a vessel containing argon or nitrogen, or a mixture of the two, for a period of at least 3 minutes.

The revealing heat treatment can also comprise a dry and/or wet thermal oxidation step performed in an atmosphere optionally containing argon, nitrogen, or a mixture of the two, in addition to oxygen. Thermal oxidation steps are followed by a deoxidation step to completely eliminate the previously-formed oxide layer. The optional deoxidation step preferably includes treatment by hydrofluoric acid (HF). When wet oxidation of the bulk substrate is used, it is preferably performed under condition so that a layer of silicon oxide ($SiO_2$) with a thickness in the range 500 nm to 900 nm is formed, for example, at a temperature in the range 500° C. to 1300° C. for a period of 3 minutes to a few tens of hours in order. When he dry oxidation of the bulk substrate is conducted it is preferably performed under conditions selected to form a layer of silicon oxide ($SiO_2$) with a thickness of a few tens of nanometers. This dry oxidation may be performed at a temperature in the range of approximately 500° C. to 1100° C. for a period of approximately 2 minutes to 15 minutes, and preferably at a temperature close to 950° C. for approximately 5 minutes.

After a first revealing heat treatment and/or after an optional deoxidation step, a further revealing heat treatment and/or defect enlargement step can be performed to enlarge defects revealed by the first revealing heat treatment. The defect enlargement step can comprise a rapid thermal process (RTP) type heat treatment, at temperatures from a few hundred degrees Celsius to approximately 1300° C. for a period in the range from a few seconds to a few minutes. In more detail, the rapid heat treatment can be of the rapid thermal anneal (RTA) type carried out in the presence of argon and/or hydrogen. Alternately, a RTA step for enlarging crystalline defects can be performed in a "batch furnace anneal" in a neutral and/or hydrogen atmosphere at temperatures of the order of 1100° C. to 1250° C. for a few minutes to a few hours.

The rapid thermal process can also be of the rapid thermal oxidation (RTO) type carried out in the presence of oxygen.

After the defect enlargement step, a silicon deposition step deposits a layer of silicon a few micrometers thick on said bulk substrate by epitaxial growth. The silicon deposition step further makes defects apparent.

In a preferred embodiment, this invention also provides defect measuring methods. The defect measuring methods measure latent defects that would appear subsequently if said substrate were to be used multiple (e.g., at least three) times in a method of lifting and transferring layers. The defect measuring methods measure latent crystalline defects in the bulk substrate that have been revealed by the defect revealing methods of this invention. The methods comprise a further step of counting revealed crystalline defects using a counter installation in order to determine the crystalline defect density per unit area in said bulk substrate. Advantageously, the counter installation comprises at least one microscope and counter apparatus, or an atomic force microscope, or a laser surface analysis device, or a light scattering tomography (LST) device, or a scanning infrared microscope (SIRM).

In a preferred embodiment, this invention also provides bulk silicon substrates for subsequent use in an SOI-type fabrication process method where multiple (e.g., at least three) layers are lifter and transferred from the bulk substrates. The provided bulk silicon substrates are selected by the methods of this invention to have crystalline defect densities of less than approximately preferably 0.1 defects per $cm^2$. Such a substrate is of particular application in the fabrication of SOI type substrates.

In a preferred embodiment, this invention also provides silicon ingot fabricating methods for fabricating bulk silicon substrates from an ingot obtained by Czochralski type pulling. These methods first predictively revealing crystalline defects in ingot segments using the defect revealing methods of this invention. Segments having an unsuitable number or type of defects are preferably not further used in a bulk substrate fabrication cycle. Further, the ingot pulling methods can be adjusted to limit the number of unsuitable segments.

Other combinations, characteristics and advantages of the invention become apparent from the following description made with reference to the accompanying drawings which indicate a possible non-limiting implementation. The term "approximately", when used herein to modify a nominal value, is used to mean within a measurement or control range of the nominal value, or alternately within 1%, or 5%, or 10% of the nominal value.

BRIEF DESCRIPTION OF THE DRAWINGS

The present invention may be understood more fully by reference to the following detailed description of the preferred embodiment of the present invention, illustrative examples of specific embodiments of the invention and the appended figures in which.

DETAIL DESCRIPTION OF THE PREFERRED EMBODIMENTS

Figure 1A:
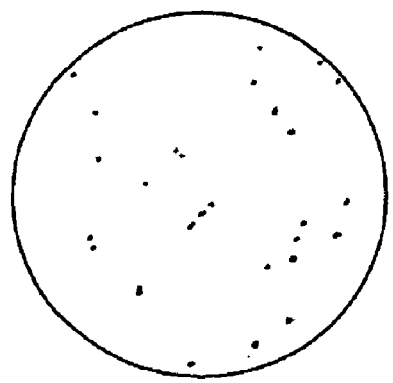
FIGS. 1A and 1B illustrate a surface of a bulk silicon substrate after a first crystalline defect revealing treatment and after a second crystalline defect revealing treatment, respectively.

One preferred his embodiment of this invention is based on the further discovery that repeatedly performing the defect revealing methods of this invention causes to successively increases their dimensions so that even small pre-existing defects can become apparent. Such defects are generally oxygen precipitates. Accordingly, in this embodiment, the methods of this invention perform a plurality, e.g., three, successive stages of analysis of reference substrates selected from a bulk silicon substrate. Each stage comprises the defect-revealing methods and/or the defect-measuring methods of this invention. so that increasingly exacting analysis of the reference substrates is performed. The reference substrates are also referred to herein as the "sample substrate". The quality of reference (equivalently, sample) substrates are usually representative of other substrates obtained from the same ingot or the same segment. It is understood, that the defect revealing and/or defect counting methods of this invention can also be performed only once on a bulk silicon substrate.

In more detail, if a first stage application of the defect revealing methods of this invention makes apparent a number or an arrangement of defects in this substrate that would be prohibitive for the envisaged application, this substrate and those which it represents (e.g., substrates from the same segment or ingot) are discarded. If the first stage reveals at most a few defects, the sample (reference) substrate can undergo a second stage application of the revealing methods of this invention. An unsuitable substrate can be discarded at this point, or can optionally undergo a third stage of analysis, and so forth. The defect measuring methods of this invention can count revealed crystalline defects.

The multistage analysis generally makes it possible to detect smaller and smaller defects. Substrates which pass two or more stages of analysis can generally be recycled at least three times, or at least six times, or perhaps twelve times without defects appearing in the lifted layers.

Defects generally become apparent only when their sizes are above the detection threshold of the defect measuring apparatus. For currently preferred apparatus, this threshold is approximately 0.13 μm. The various levels of analysis are thus aimed at enlarging the defects present until they reach this minimum dimension.

First Stage of Analysis

The first analysis stage of a bulk substrate begins with a first revealing heat treatment. A bulk substrate, whether virgin or already recycled, already contains oxygen. If the bulk substrate has been subjected to heat treatments between approximately 500° C. and 900° C., the oxygen is present in the form of agglomerates or nuclei. If a revealing heat treatment is then performed at temperatures in the range 900° C. to 1300° C., the agglomerates or nuclei can grow and become transformed into large precipitates which can then be observed and counted (i.e., the revealing heat treatment is at a temperature above the temperature of previous heat treatments). The duration of a revealing heat treatment period should be adjusted as a function of the temperature applied during the heat treatment, and also adjusted as a function of the nature of the substrate, e.g., virgin or recycled. The heat treatment period should be longer if the substrate is intended for a greater number of cycles of reuse. As an example, a substrate representative of substrates which are intended to be recycled eight times will be heated for a longer period than if only three recycles were envisaged.

In one preferred embodiment, the revealing heat treatment can be preferably performed in a non-reducing atmosphere at a temperature in the range from approximately 500° C. to approximately 1300° C., preferably in the range 900° C. to 1300° C. The revealing heat treatment can be performed in a vessel containing a gas mixture comprising at least 10 ppm of oxygen (based on the whole volume of the gaseous mixture present in the vessel) and argon, or nitrogen, or a mixture of these two gases. The heat treatment can be performed for a duration of least 3 minutes to a few tens of hours, preferably for 6 h at a temperature of approximately 950° C.

Optionally, before any revealing heat treatment, the bulk silicon substrates can undergo light oxidation (dry oxidation) to generate a fine layer of silicon oxide ($SiO_2$) of the order of ten nanometers thick. This dry oxidation can be performed at a temperature in the range approximately 500° C. to 1100° C. for a period of approximately 2 minutes to 15 minutes, preferably at a temperature of close to approximately 950° C., for approximately 5 minutes. If dry oxidation step is performed, a subsequent revealing heat treatment can be conducted in an oxygen free atmosphere. This oxidation step in intended to provide a surface quality which is as perfect as possible Oxide layers that have been formed during heat treatments are preferably removed (referred to herein as "deoxidation") before defects and counted. Complete deoxidation of the substrate can be carried out with, e.g., hydrofluoric acid (HF). An aqueous 8% solution of hydrofluoric acid can be used for approximately 15 minutes. The conditions for deoxidation (concentration, treatment period) with HF acid are adapted as a function of the thickness of the layer to be eliminated. This step selectively etches the oxide layer to provide access to the silicon surface to be analyzed.

In one preferred embodiment, the revealing heat treatment can comprise a dry and/or wet thermal oxidation of the substrate, carried out in an atmosphere optionally comprising, in addition to oxygen, the gases argon, or nitrogen, or a mixture of the two gases. This thermal oxidation step can make apparent zones of a bulk substrate that can become small-sized or medium-sized defects at the interface between the bulk silicon and the layer of silicon oxide in a subsequently fabricated SOI substrate. This thermal oxidation step can be performed in a single step, and also in several successive oxidation steps, to obtain the same result in the end.

Wet oxidation allows a thick (of the order of a few hundreds of nanometers) layer of silicon oxide ($SiO_2$) to be formed. The oxidation temperature and duration parameters should be adapted to obtain the desired final thickness. In a particular application of the invention, the parameters are adjusted to obtain a layer 500 nm to 900 nm thick. When dry oxidation is performed, it occurs under the same conditions as those described above. For example, dry oxidation can be carried out in a single step between 800° C. and 1000° C. for 6 hours to form a layer of silicon oxide having a thickness of the order of a few hundreds of nanometers, e.g., 730 nm. Alternately, dry oxidation can be carried out in a plurality of, e.g., seven, steps at 950° C. of 1 hour duration, each step forming a layer of silicon oxide having a thickness of the order of one to two hundred nanometers, e.g., 140 nm thick. Dry oxidation can be performed in place of wet oxidation or alternately before and/or after wet oxidation. A final deoxidation step is as elsewhere described is then performed.

At the end of this first stage of analysis, the revealed defects that have a mean diameter of at least 0.13 μm can be observed and counted. Defects of less than 0.13 μm are not visible. Substrates which have few or no defects apparent after a first analysis stage preferably undergo second analysis stage, or even a third analysis stage. A further analysis stage can further enlarge latent defects not yet visible at the current analysis stage, thereby checking whether defects are still too small to be revealed.

Second Stage of Analysis

A second analysis stage enlarges defects not revealed by the first analysis stage. The second analysis stage can include either rapid thermal processing or batch heat treatment.

Rapid thermal processing (referred to herein as "RTP") type treatments include treatments known as "RTA" (rapid thermal annealing) and treatments known as "RTO" (rapid thermal oxidation). RTA processes are performed in an atmosphere of argon and/or hydrogen (in the absence of oxygen). RTO processes are performed in the presence of oxygen. RTP processes can also be defect revealing heat treatments.

Rapid thermal processing (referred to herein as "RTP") is preferably conducted in a rapid anneal furnace. Rapid thermal anneal furnaces permit temperature ramp-up and ramp-down at rates of more than several tens of degrees Celsius per second, and allow the substrate to be heated to temperatures from a few hundred degrees Celsius, preferably approximately 300° C., to approximately 1300° C., with treatment periods from a few seconds to a few minutes. Such furnaces are sold by, e.g., Applied Materials under the trade name Centura.

Batch heat treatments (also referred to as a "batch anneal" process) are performed in an atmosphere of a neutral gas (argon or nitrogen) and/or hydrogen, at temperatures of the order of 1100° C. to 1250° C., for a few minutes to a few hours.

At the end of a second analysis stage, defects revealed that have a mean diameter of more than 0.13 µm can then be observed and counted. In contrast, latent defects still having of mean diameter of less than 0.13 µm are still not visible. Substrates having few or no visible defects at the end of the second analysis stage preferably then undergo a third analysis to enlarge not yet apparent defects.

Third Stage of Analysis

A third analysis stage comprises epitaxial growth of a layer of silicon on the bulk substrate. This epitaxial silicon layer enlarges and makes apparent defects that are too small to be visualized. The epitaxial layer reproduces the previously-revealed defects, in particular by reproducing the lattice arrangements of the underlying substrate to be analyzed. This epitaxial growth step maybe carried out with, e.g., a dichlorosilane type precursor, to a thickness of preferably the order of a few micrometers.

Optionally, further stages of analysis can be performed on a bulk silicon substrate.

Defect Measurement

Subsequent to the one or more stages of analysis, the density of revealed crystalline defects per unit area is measured using a counter installation. Preferably, the counter installation can also detect particles and surface defects or even analyze surface roughness. Most equipment which can detect defects on a bulk silicon substrate can be used for defect measurement. For example, a counter installation can include a microscope and a counter device, or an atomic force microscope (AFM), or a laser surface analysis device, or similar.

In particular, a counter installation can include an optical microscope that can detect crystalline defects which have been revealed, and a counter device to measure detected defects. In one embodiment, an operator can detect and count defects in one or more zones of the sample, and can then deduce therefrom the crystalline defect density. In another embodiment, the counter installation can be automated. For example, the microscope can be combined with an automatic system for detecting the revealed crystalline defects, for example by image processing, and/or a system for automating the displacement of the sample, in order to define and scan the observed surface.

Another example of a counter installation can include a laser surface analysis device. Such a device is sold under the trade name "Surfscan" (e.g., model 6200, or SP1) by KLA-Tencor. A laser surface analysis device can provide not only the number of revealed defects, but can also provide defect maps illustrating the geographical distribution of defects over the surface of each wafer (bulk silicon substrate).

Another example of a counter installation includes apparatus which can not only count surface defects but also can analyze defect depth, thereby obtaining information concerning defect volume. Such equipment includes light scattering tomography apparatus (LST) or a scanning infrared microscope (SIRM).

EXAMPLE

The figures illustrate surface defect distributions on 300 mm diameter silicon wafers (substrates) observed and detected by a Surfscan SP1 device after the wafers have undergone one or more defect-revealing treatment. The first defect revealing treatment includes a heat treatment conducted at a temperature of the order of 950° C. for 6 hours in the presence of oxygen and hydrogen. The second defect revealing treatment includes epitaxial growth of a 2 µm thick layer of silicon over each silicon wafer. The wafers are then classified as being of good or poor quality as a function of the number of defects present on the surface of a wafer (bulk silicon or virgin substrate) and also as a function of geographical distribution of defects over each wafer.

Figure 1B:
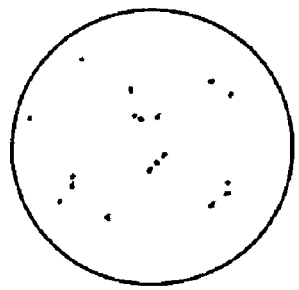

The wafer illustrated in FIGS. 1A and 1B is classified as good quality. FIG. 1B illustrates that even after a second defect revealing treatment (including epitaxial silicon growth), the revealed number of defects is small and uniformly distributed.

Figure 2:
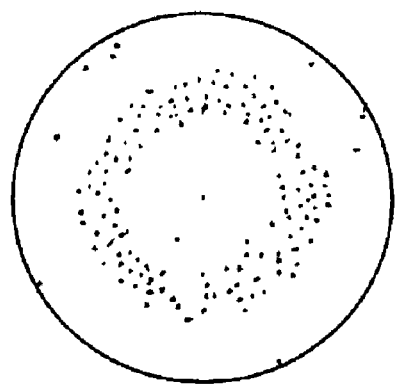
FIG. 2 illustrates a surface of a further bulk silicon substrate after a first crystalline defect revealing treatment.

The wafer illustrated in FIG. 2 is not classified as good quality mainly because of a prohibitive number of defects. After a first defect revealing treatment, a prohibitive number of defects are apparent and are arranged in a ring.

Figure 3A:
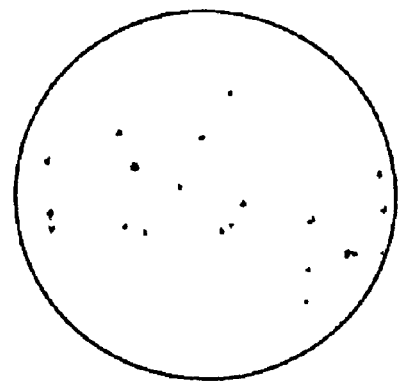
FIGS. 3A and 3B illustrate a surface of a further bulk silicon substrate after a first crystalline defect revealing treatment and after a second crystalline defect revealing treatment, respectively.
Figure 3B:
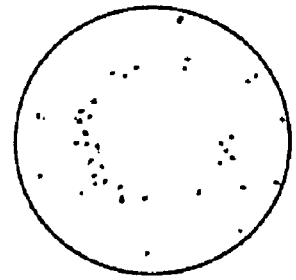

The wafer illustrated in FIGS. 3A and 3B is also not classified as good quality mainly because of an unfortunate geographical arrangement of defects. The first defect revealing treatment makes apparent only a small number of uniformly distributed defects. However, the second defect revealing treatment (including epitaxial silicon growth) makes apparent that, although the number of defects present is still relatively small, they are apparently concentrated in a ring-shaped zone.

Headings are used herein for clarity only and without any intended limitation. The preferred embodiments of the invention described above do not limit the scope of the invention, since these embodiments are illustrations of several preferred aspects of the invention. Any equivalent embodiments are intended to be within the scope of this invention. Indeed, various modifications of the invention in addition to those shown and described herein, such as alternate useful combinations of the elements described, will become apparent to those skilled in the art from the subsequent description. Such modifications are also intended to fall within the scope of the appended claims. In the following (and in the application as a whole), headings and legends are used for clarity and convenience only.

What is claimed is:

1. A method for selecting a bulk silicon substrate of suitable quality for use in a subsequent semiconductor fabrication process, the method comprising:

performing a revealing heat treatment on a reference silicon substrate in order to predictively reveal crystalline defects in the reference substrate, the reference silicon substrate selected to have a quality representative of the quality of the bulk silicon substrate, wherein the revealing heat treatment comprises heat treatment conducted in a non-reducing atmosphere at a temperature from approximately 500° C. to approximately 1300° C., determining a quality of the reference substrate in dependence on the number of, and the geographical arrangement of, defects apparent on the surface of the processed reference substrate, and selecting the bulk substrate for use in a subsequent semiconductor fabrication process in dependence on the determined quality of the reference substrate and on the requirements of the subsequent fabrication process;

wherein the fabrication process is a silicon-on-insulator process which comprises oxidizing at least a first surface of a bulk substrate to form an insulation layer, implanting atomic species into the bulk substrate to form a zone of weakness that defines a useful layer to be transferred with the insulation layer, bonding the insulation layer of the bulk substrate to a receiving substrate; and detaching the useful layer and insulation layer at the zone of weakness to transfer those layers to the receiving substrate, with the fabrication process repeated a desired number of times on the selected bulk substrate to transfer one or more additional useful layers to other receiving substrate(s).

2. The method of claim 1 wherein quality of the reference substrate is suitable for a fabrication process which separates and transfers at least three surface layers from the bulk substrate to receiving substrates.

3. The method of claim 1 wherein both the reference substrate and the bulk substrate are obtained by slicing from the same ingot.

4. The method of claim 3 wherein both the reference substrate and the bulk substrate are sliced from the same segment of the same ingot.

5. The method of claim 4 wherein the reference substrate is sliced from a region closer to the end of the segment than the region from which is sliced the bulk substrate.

6. The method of claim 1 wherein the revealing heat treatment further comprises exposure to at least approximately 10 ppm of oxygen and one or more of argon or nitrogen for up to at least 3 minutes up to approximately 6 hours at a temperature close to 950° C.

7. The method of claim 1 wherein the revealing heat treatment further comprises:

performing dry oxidation, or a wet oxidation, or both a dry and a wet oxidation of the reference substrate; and deoxidizing of the reference substrate subsequently to the oxidation step.

8. The method of claim 7 wherein a wet oxidation is performed under the conditions selected to form a layer of silicon oxide ($SiO_2$) of a thickness in the range 500 nm to 900 nm.

9. The method if claim 7 wherein a dry oxidation is performed under the conditions selected to form a layer of silicon oxide ($SiO_2$) with a thickness of a few tens of nanometers.

10. The method of claim 9 wherein the dry oxidation is performed at a temperature in the range of approximately 500° C. to 1100° C. for a period of approximately 2 minutes to 15 minutes.

11. The method of claim 9 wherein the dry oxidation is performed at a temperature close to 950° C. for approximately 5 minutes.

12. The method of claim 9 wherein the dry oxidation is performed prior to the revealing heat treatment and the deoxidizing is performed subsequent to the revealing heat treatment.

13. The method of claim 7 wherein deoxidizing comprises exposure to hydrofluoric acid (HF).

14. The method of claim 1 comprising performing on the reference substrate prior to the selecting step a further revealing heat treatment comprising one or more of the following further processes:

a further heat treatment process at a temperature from approximately 500° C. to approximately 1300° C. for a period up to approximately 6 hours in a non-reducing atmosphere or in a neutral or hydrogen atmosphere, a rapid thermal process (RTP) conducted at temperatures from approximately 300° C. to approximately 1300° C. for a period up to approximately 10 minutes, and an epitaxial growth process depositing a layer of silicon up to 10 micrometers thick on said reference substrate.

15. The method of claim 14 wherein the RTP further comprises a rapid thermal annealing (RTA) process performed in an atmosphere including one or more of argon or hydrogen.

16. The method of claim 14 wherein the RTP further comprises a rapid thermal oxidation (RTO) performed in an atmosphere including oxygen.

17. The method of claim 14 further comprising, subsequent to performing the further revealing heat treatment, determining again a quality of the reference substrate in dependence on the number of, and the geographical arrangement of, defects apparent on the surface of the processed reference substrate.

18. The method of claim 1 wherein the quality of the reference substrate is determined by counting the revealed crystalline defects per unit area using a counter installation to determine the crystalline defect density in said bulk substrate, and the bulk substrate is selected for use in a subsequent semiconductor fabrication process depending upon the counted crystalline defects and on the requirements of the subsequent fabrication process.

19. The method of claim 18 wherein the counter installation further comprises one or more of a microscope and a counter apparatus, an atomic force microscope; a laser surface analysis device; a light scattering tomography apparatus (LST), and a scanning infrared microscope (SIRM).

20. The method of claim 18 wherein the bulk silicon substrate selected has less than approximately 0.1 defects per $cm^2$.

21. The method of claim 18 comprising performing on the reference substrate prior to the selecting step:

a further revealing heat treatment comprising one or more of the following further processes:

a dry oxidation process, or a wet oxidation process, or both a dry and a wet oxidation processes of the reference substrate and deoxidizing of the reference substrate subsequently to the oxidation step;

a further heat treatment process at a temperature from approximately 500° C. to approximately 1300° C. for a period up to approximately 6 hours in a non-reducing atmosphere or in a neutral or hydrogen atmosphere, a rapid thermal process (RTP) conducted at temperatures from approximately 300° C. to approximately 1300° C. for a period up to approximately 10 minutes, and an epitaxial growth process depositing a layer of silicon up to 10 micrometers thick on said reference substrate; and a further defect counting step using the counter installation.

22. The method of claim 1 wherein the bulk substrate is provided from an ingot obtained by Czochralski type pulling, both the bulk substrate and reference substrate are obtained by slicing from the ingot, with the reference silicon substrate selected to have a quality representative of the quality of the bulk silicon substrate.

23. The method of claim 22 wherein both the reference substrate and the bulk substrate are sliced from the same segment of the same ingot, the reference substrate being sliced from a region closer to the end of the segment than the region from which is sliced the bulk substrate.

* * * * *